United States Patent [19]

Olah

[11] 4,373,109

[45] Feb. 8, 1983

[54] BIFUNCTIONAL ACID-BASE CATALYZED CONVERSION OF HETERO-SUBSTITUTED METHANES INTO OLEFINS

[76] Inventor: George A. Olah, 2252 Gloaming Way, Beverly Hills, Calif. 90210

[21] Appl. No.: 290,292

[22] Filed: Aug. 5, 1981

[51] Int. Cl.[3] ................................................ C07C 1/00
[52] U.S. Cl. .................................... 585/640; 585/638; 585/639; 585/641; 585/642; 585/733
[58] Field of Search ............... 585/639, 640, 641, 642, 585/733, 638

[56] References Cited

U.S. PATENT DOCUMENTS

| | | | |
|---|---|---|---|
| 4,072,732 | 2/1978 | Hargis et al. | 585/639 |
| 4,247,731 | 1/1981 | Wunder et al. | 585/640 |
| 4,254,297 | 3/1981 | Frenken et al. | 585/733 |
| 4,296,266 | 10/1981 | Wunder et al. | 585/640 |

*Primary Examiner*—Curtis R. Davis
*Attorney, Agent, or Firm*—Pennie & Edmonds

[57] ABSTRACT

This invention discloses a process for converting heterosubstituted methanes, such as methyl alcohol, methyl ether, methyl mercaptan, dimethyl sulfide, methyl halides, methylal, methylamine and the like, by contacting such methanes with bifunctional acid-base catalysts at elevated temperatures, between 200° and 450° C., preferably between 250° and 375° C., to produce predominantly lower olefins, preferably ethylene and propylene. The catalysts of preference are those derived from halides, oxyhalides, oxides, sulfides or oxysulfides of transition metals of Groups IV, V, VI, VIII of the Periodic Table, such as tantalum, niobium, zirconium, tungsten, titanium, chromium and the like, deposited on acidic oxides and sulfides such as alumina, silica, zirconia or silica-alumina.

17 Claims, No Drawings

BIFUNCTIONAL ACID-BASE CATALYZED CONVERSION OF HETERO-SUBSTITUTED METHANES INTO OLEFINS

TECHNICAL FIELD

This invention discloses a process for converting heterosubstituted methanes, such as methyl alcohol, methyl ether, methyl mercaptan, dimethyl sulfide, methyl halides, methylal, methylamine and the like, by contacting such methanes with bifunctional acid-base catalysts at elevated temperatures, between 200° and 450° C., preferably between 250° and 375° C., to produce predominantly lower olefins, preferably ethylene and propylene. The catalysts of preference are those derived from halides, oxyhalides, oxides, sulfides or oxysulfides of transition metals of Groups IV, V, VI, VIII of the Periodic Table, such as tantalum, niobium, zirconium, tungsten, titanium, chromium and the like, deposited on acidic oxides and sulfides such as alumina, silica, zirconia or silica-alumina.

BACKGROUND ART

The conversion of methyl alcohol or dimethyl ether into open chain hydrocarbons of the gasoline range, as well as of cyclic aromatic nature, is of recent substantial significance in the context of the utilization of inexpensive starting materials, which can be produced from a variety of sources, including coal, wood products, natural gas or other sources of methane gas, including any source of bio-mass.

A century ago, LeBel and Greene first reported (Beilstein, Vol. 1, p. 277 (1918)) the production of gaseous saturated hydrocarbons (and some hexamethylbenzene) by adding methyl alcohol dropwise to "hot" zinc chloride. Grosse in U.S. Pat. No. 2,492,984 described the formation of hydrocarbons from methyl alcohol over zinc chloride at 400° to 425° C. and pressures ranging from 1,000 to 2,500 psi. Kim et al. recently reported (J. Org. Chem., 43, 3432 (1978)) that when methyl alcohol was reacted with a large excess of zinc iodide or bromide at 200° C. under 200 psi of nitrogen, a mixture of $C_4$ to $C_{13}$ hydrocarbons containing almost 50% of 2,2,3-trimethylbutane (triptane) was obtained. This unusual selectivity was considered to be the consequence of a carbenoid-type mechanism involving organozinc (Simmons-Smith type) complexed carbene intermediates.

The conversion of dimethyl ether mixed with "a normally gaseous alkane generally isobutane" over a silica-alumina catalyst at 350° to 400° C. and 10–800 psi has been reported in U.S. Pat. No. 2,456,584; a mixture of normally liquid hydrocarbons, predominantly of the isoparaffinic and aromatic types, was obtained.

Supported aluminum sulfate has also been used for the conversion of methyl alcohol and dimethyl ether into higher hydrocarbons by contacting them at 250° to 400° C. as described in U.S. Pat. No. 4,072,733. The overall conversion was, however, low.

Alcohols of two or more carbon atoms produce a variety of hydrocarbons using polyphosphoric acid or other dehydrating agents at elevated temperature and pressure, as described for example in U.S. Pat. No. 2,373,475.

Pearson in U.S. Pat. No. 4,133,838 describes the conversion of methyl alcohol or trimethyl phosphate to hydrocarbons using phosphorus pentoxide or polyphosphoric acid in molar quantity as condensing agent. A wide range of hydrocarbons (about 200 compounds) are formed in 36 to 39% yield. The transformations have been explained by $\beta$-elimination followed by condensation or polymerization of the olefin to higher hydrocarbons.

The Mobil Oil Company in recent years disclosed a new type of shape selective catalytic processes using the acidic form of a particular type of alumino-silicate molecular sieve catalysts called ZMS-zeolites, such as ZMS-5 as described in U.S. Pat. No. 3,702,886, for the conversion of methyl alcohol into gasoline-range hydrocarbons. The process has been described in a number of patents, such as U.S. Pat. Nos. 3,894,106, 3,894,107, 3,928,483. The key to the process is stated to be the favorable shape selectivity of the catalyst allowing zeolite conversion to take place in the cavities and channels of intermediate pore size. For example, Chang and Silvestri in the J. Catalysis, 47, 249 (1977) described in detail the overall shape selective Mobil conversion of methyl alcohol into hydrocarbons, proposing a carbenoid-type mechanism to account for the initial step of the overall process. Derouane et al. elucidated other aspects of the mechanism using $^{13}C$ NMR studies, proposing a propagating carbocation mechanism to explain most of the products obtained (J. Catalysis, 53, 40 (1978)).

The ZMS-5 technology disclosed by Mobil originally was for the production of liquid hydrocarbon mixtures of the gasoline range; subsequently, as described in U.S. Pat. No. 3,911,041, a modified zeolite catalyst containing phosphorus incorporated within the crystal structure, was described as producing from methyl alcohol or dimethyl ether products rich in olefins. These catalysts were also further modified by impregnation with zinc. Similar results were described with manganese impregnated zeolites as in DOS No. 2,755,229 (1979, Hoechst).

SUMMARY OF THE INVENTION

The present invention relates to the discovery that heterogeneous supported bifunctional acid-base catalysts, particularly those derived from halides, oxyhalides, oxides, sulfides and oxysulfides of transition metals of Groups IV, V, VI, VIII of the Periodic Table, such as of tantalum, niobium, zirconium, tungsten, titanium, chromium and the like, or mixtures thereof, or deposited on suitable carriers, such as alumina, zirconia or silica-aluminia, are capable of effecting the ready conversion of heterosubstituted methanes, such as methyl alcohol, methyl ether, methyl mercaptan, dimethyl sulfide, methyl halides, methylal, methylamine and the like, into higher hydrocarbon mixtures containing predominantly $C_2$ to $C_5$ olefins, primarily ethylene and propylene, at temperatures between 200° and 450° C., preferably between 250° and 375° C. These catalysts do not possess the oriented structure considered essential in shape selective zeolite type catalysts; also, these catalysts cannot give rise to Simmon-Smith type of zinc-carbenoid complexes. Thus, these catalysts represent an independent novel type of catalyst for the conversion of heterosubstituted methanes into hydrocarbons. I believe that these catalysts act through their acidic-basic bifunctional nature, first forming on the surface via acid catalysis an onium ion, such as trimethyl oxonium ion, which subsequently through the basic nature of the catalyst is transferred into a highly reactive surface-complexed ylid, such as methylenedimethyl oxonium ylid, which then in the presence of excess heterosubstituted methane is exceedingly readily transferred into ethylene. I believe all further products of the process are subsequently formed from ethylene.

As noted in Olah, G. A. "Friedel-Crafts Chemistry," N.Y., Wiley-Interscience, 1973. p. 343-344, the elements of Groups VIA have been called "chalcogens", and compounds containing these elements are called "chalconites", "chalcogenides" or "chalcides." Acidic oxide and sulfide catalysts are termed "acidic chalcogenide catalysts", and include a variety of solid oxides and sulfides, especially those comprising alumina, silica and mixtures of alumina and silica, either natural or synthetic, in which other oxides such as chromia, magnesia, molybdena, thoria, tungstic oxide, zirconia, etc., may also be present, as well as sulfides of molybdenum. Many compositions exist for possible use as catalysts including: bauxite, floridin, Georgia clay, and other natural aluminosilicates, the composition and certain features of structure of which are still not well known.

Synthetic catalysts, other than those of the silica-alumina type, representative of the acidic chalcide group are: $BeO$, $Cr_2O_3$, $P_2O_5$, $ThO_2$, $TiO_2$, $Al_2(SO_4)_3$ (which may be regarded as $Al_2O_3.3SO_3$), $Al_2O_3 \cdot Cr_2O_3$, $Al_2O_3 \cdot Fe_2O_3$, $Al_2O_3 \cdot CoO$, $Al_2O_3 \cdot MnO$, $Al_2O_3 \cdot Mo_2O_3$, $Al_2O_3 \cdot V_2O_3$, $Cr_2O_3 \cdot Fe_2O_3$, $MoS_2$, and $MoS_3$.

The acidic chalcides are physically and chemically stable. Although they are catalytically active at temperatures close to the threshold of thermal decomposition of hydrocarbons, their acidity is not great enough to lead them to form stable complexes with unsaturated hydrocarbons, as do the aluminum halides, for example.

For these reasons, the chalcide catalysts are frequently used at higher temperatures and have been preferred for isomerization of unsaturated hydrocarbons, which are polymerized by strongly acidic catalysts at lower temperatures. Polymerization is thermodynamically relatively unfavorable at higher temperatures.

BEST MODE FOR CARRYING OUT INVENTION

The process of this invention is carried out by reacting the corresponding heterosubstituted methane derivative with the bifunctional acid-base catalyst in a fixed-bed, fluid-bed or tubular reactor. These reactors are well known to those skilled in the art of heterogeneous catalytic reactions.

When methyl alcohol is the feed, the first step of the conversion is the reversible dehydration of methyl alcohol to dimethyl ether. This step, is generally slower over the described catalysts than the subsequent olefin forming condensation, and can also be carried separately over an acidic catalyst, such as a solid superacidic perfluorinated sulfonic acid (Nafion-H or a supported $R_FSO_3H$ catalyst of eight to eighteen carbon atoms). The dimethyl ether formed is separated from the water produced and introduced into the olefin condensation reactor.

When methyl halides are used as the feed, hydrogen halides are by-products of the condensation, and upon separation they can be recycled for halogenation of methane under conditions of my copending application Ser. No. 298,390. Methane (and ethane) formed as by-products of the condensation can be recycled for selective halogenation or oxidation under conditions of my co-pending applications Ser. Nos. 298,390 and 298,486, substantially improving the conversion and efficiency of the process.

When methyl mercaptan or dimethyl sulfide are used as the feed, hydrogen sulfide is a by-product of the condensation and it can be also recycled for regeneration of sulfur.

Typical examples of the hydrocarbon distributions obtained from the reaction of methyl alcohol or dimethyl ether over the aforementioned catalysts are given in the Examples and results summarized in Table I. Methyl alcohol and dimethyl ether give practically identical results. The initial dehydration step with methyl alcohol can also be carried out separately by processes effecting such dehydrative methyl ether formation, generally over acidic catalysts including solid superacid catalysts of the perfluorinated sulfonic acid-type.

The novel, bifunctional acid-base catalyzed conversion of this invention provides significant advantages, as exemplified in the examples, in the production of mixtures of predominantly lower ($C_2$ to $C_5$) olefins containing some saturated hydrocarbons. The catalysts are easily regenerated by oxidative treatment and provide a convenient means of converting of substituted methane derivatives into lower olefins. Methane formed as by-product can be recycled in accordance with processes disclosed in my co-pending application Ser. No. 298,486 and thus economically utilized.

EXAMPLES

The following Examples are illustrative of the invention, are set forth for the purpose of illustration only and are not to be construed as limiting the scope of the invention in any manner. In the related Table I product compositions are given; the compositions have been normalized, even if not so stated, to provide a total conversion of 100 percent.

EXAMPLE 1

This Example illustrates the conversion of methyl alcohol by the process of the invention. Supported tungsten oxide was prepared by impregnating $Al_2O_3$ with an aqueous solution of ammonium tungstate. After evaporation of water, the catalyst was dried in air at 105° to 115° C. and calcined at 480° to 550° C. for 5 hours.

10 g of supported tungsten oxide on alumina catalyst (10% of the metal oxide by weight) previously calcined at 450° to 550° C. was placed in a stream of dry nitrogen into a catalytic flow reactor, such as that described, for example, by Olah and Kaspi in the *Nouveau Journal de Chimie*, Vol. 2, p 585 (1978). Methyl alcohol in the gaseous phase was passed over the supported catalyst in the reactor at a temperature of 325° C. with a gaseous space velocity (the gaseous space velocity being defined at volume of gas passed over volume catalyst per hour) of 50. The results obtained are given in Table I, as weight percent of the effluent stream from the reactor.

EXAMPLE 2

This Example illustrates the conversion of dimethyl ether under conditions similar to those of Example 1. The results obtained are described in Table I.

EXAMPLE 3

Tantalum pentafluoride was slowly stirred into cold methyl alcohol ($-78°$ to $-10°$ C.) with evolution of some hydrogen fluoride. A suitable alumina carrier was then treated with the solution so that subsequent heating to 200° to 300° resulted in 10% tantalum oxyfluoride deposited on the alumina. 10 g of this catalyst was then charged into the catalytic reactor and reacted with dimethyl ether under the conditions shown in Table I.

EXAMPLE 4

This Example illustrates the conversion of dimethyl ether over tungsten oxide supported on zirconia. The catalyst was prepared as described in Example 1, but deposited on zirconia. A decreased amount of methane formation as compared to Example 2 using alumina as support was obtained as reported in Table I.

EXAMPLE 5

Zirconium tetrafluoride was dissolved in methyl alcohol and deposited on alumina as in Example 3. The conversion of dimethyl ether was carried out as in previous examples and the conditions and results are reported in Table I.

EXAMPLE 6

Ceric oxide deposited on alumina was used as the catalyst in the conversion of dimethyl ether. The results and conditions of this experiment are described in Table I.

EXAMPLE 7

This Example shows the adaptability of the process to dimethoxymethane (methylal) with results similar to those of Example 2. The results and conditions are described in Table I.

EXAMPLE 8

Dimethyl sulfide under conditions of Example 2 undergoes condensation. Methyl mercaptan formed in 20% yield can be recycled. The results and conditions employed in this Example are described in Table I.

EXAMPLES 9 AND 10

Methyl halides, such as methyl fluoride and methyl chloride respectively, are well adaptable under the conditions of Example 2 to the olefin forming process. The conditions and results of these experiments are described in Table I.

TABLE I

| Example | 1 | 2 | 3 |
|---|---|---|---|
| Reactant | $CH_3OH$ | $CH_3OCH_3$ | $CH_3OCH_3$ |
| Catalyst | $WO_3$ on alumina | $WO_3$ on alumina | Tantalum oxyfluoride on alumina |
| Temperature °C. | 325 | 322 | 250 |
| % conversion (per pass) | 99 | 99 | 25 |
| Prod. distribution % | | | |
| methane | 27.4 | 21.3 | 14.2 |
| ethane | 0.9 | 1.3 | 3.3 |
| ethylene | 32.2 | 28.2 | 22.6 |
| propane | trace | 1.3 | 2.4 |
| propylene | 31.3 | 30.4 | 25.7 |
| butanes | 5.2 | 6.3 | 12 |
| butylene | 3.0 | 8.7 | 13.6 |
| $C_5$ | trace | 2.5 | 6.2 |
| highers | trace | 8 | trace |

| Example | 4 | 5 | 6 |
|---|---|---|---|
| Reactant | $CH_3OCH_3$ | $CH_3OCH_3$ | $CH_3OCH_3$ |
| Catalyst | $WO_3$ on zirconia | zirconium tetrafluoride on alumina | ceric oxide on alumina |
| Temperature °C. | 320 | 370 | 360 |
| % conversion (per pass) | 99 | 86 | 75 |
| Prod. distribution % | | | |
| methane | 12 | 25.6 | 36.4 |
| ethane | 1.6 | 8.0 | 2.9 |
| ethylene | 28.3 | 20.9 | 18.5 |
| propane | 7.2 | 3.8 | 8 |
| propylene | 26.3 | 19.6 | 13 |
| butanes | 7.8 | 13.1 | 8.1 |
| butylene | 6.9 | 5.6 | 8.3$C_5$ |
| highers | 10.5 | 3.2 | 4.1 |

| Example | 7 | 8 |
|---|---|---|
| Reactant | $CH_2(OCH_3)_2$ | $CH_3SCH_3$ |
| Catalyst | $WO_3$ on alumina | $WO_3$ on alumina |
| Temperature °C. | 350 | 380 |
| % conversion (per pass) | 100 | 32 |
| Prod. distribution % | | |
| methane | 16.2 | 34 |
| ethane | 2.2 | 1 |
| ethylene | 24.1 | 15 |
| propane | 1.7 | trace |
| propylene | 26.3 | 27 |
| butanes | 5.5 | |
| butylene | 24 | 2.5 |
| $C_5$ | trace | |

| Example | 9 | 10 |
|---|---|---|
| Reactant | $CH_3F$ | $CH_3Cl$ |
| Catalyst | $WO_3$ on alumina | $WO_3$ on alumina |
| Temperature °C. | 329 | 327 |
| % conversion (per pass) | 99 | 36 |
| Prod. distribution % | | |
| methane | 14.5 | 34.6 |
| ethane | 1.5 | 2.5 |
| ethylene | 33.2 | 17.4 |
| propane | 3.2 | 4.2 |
| propylene | 24.9 | 15.4 |
| butanes | 13.3 | 11.5 |
| butylene | 6.0 | 12.3 |
| $C_5$ | 3.2 | 2.5 |

I claim:

1. A process for the conversion of heterosubstituted methanes at a temperature of about 250° to 400° C. over a heterogeneous supported bifunctional acid-base catalyst comprising a halide, oxyhalide, oxide, sulfide or oxysulfide of a transition metal of Groups IV, V, VI, VIII of the Periodic Table supported on an acidic chalcogenide to produce a hydrocarbon mixture of predominantly lower $C_2$ to $C_5$ olefins.

2. The process of claim 1 wherein methanol is contacted with said catalysts.

3. The process of claim 1 wherein dimethyl ether is contacted with said catalysts.

4. The process of claim 1 wherein dimethoxymethane (methylal) is contacted with said catalysts.

5. The process of claim 1 wherein methyl mercaptan is contacted with said catalysts.

6. The process of claim 1 wherein dimethyl sulfide is contacted with said catalysts.

7. The process of claim 1 wherein methyl fluoride is contacted with said catalysts.

8. The process of claim 1 wherein methyl chloride is contacted with said catalysts.

9. The process of claim 1 wherein methylamine is contacted with said catalysts.

10. The process of claim 1 wherein the heterogeneous supported acid-base catalyst is tungsten oxide on alumina.

11. The process of claim 1 wherein the heterogeneous supported catalyst is tungsten oxide on zirconia.

12. The process of claim 1 wherein the heterogeneous supported catalyst is tungsten oxide on silica.

13. The process of claim 1 wherein the heterogeneous supported catalyst is a halide of tantalum, niobium, zirconium, titanium, or chromium.

14. The process of claim 1 wherein the heterogeneous supported catalyst is an oxyhalide of tantalum, niobium, zirconium, titanium or chromium.

15. The process of claim 1 wherein the heterogeneous supported catalyst is a sulfide of tantalum, niobium, zirconium, titanium or chromium.

16. The process of claim 1 wherein the heterogeneous supported catalyst is an oxysulfide of tantalum, niobium, zirconium, titanium or chromium.

17. The process of one of claims 13, 14, 15, or 16, wherein the supports comprise alumina, silica, silicaalumina or zirconia.

* * * * *